United States Patent [19]

Hou et al.

[11] Patent Number: 4,690,891
[45] Date of Patent: Sep. 1, 1987

[54] METHOD AND THE MICROORGANISM AND ENZYME USED THEREIN FOR DEGRADING THE XANTHAN MOLECULE

[75] Inventors: Ching-Tsang Hou, Edison; Nancy P. Barnabe, Annandale, both of N.J.

[73] Assignee: Exxon Research and Engineering Company, Florham Park, N.J.

[21] Appl. No.: 774,971

[22] Filed: Sep. 11, 1985

[51] Int. Cl.$^4$ .................. C12P 39/00; C12N 9/42; C12N 1/20; C12R 1/07
[52] U.S. Cl. ...................................... 435/42; 435/209; 435/253; 435/832
[58] Field of Search .................. 435/42, 104, 274, 209, 435/253

[56] References Cited

U.S. PATENT DOCUMENTS

| | | | |
|---|---|---|---|
| 4,410,625 | 10/1983 | Cadmus | 435/42 |
| 4,416,990 | 11/1983 | Rinaudo et al. | 435/104 |
| 4,431,734 | 2/1984 | Rinaudo et al. | 435/104 |

OTHER PUBLICATIONS

Sutherland, Journal of Applied Bacteriology, 1982, vol. 53, pp. 385–393.

*Primary Examiner*—Lionel M. Shapiro
*Attorney, Agent, or Firm*—Ronald D. Hantman

[57] ABSTRACT

The present invention is a method and the microorganism and enzyme used therein to degrade the Xanthan molecule. The microorganism is a soil bacterium, Bacillus sp. The method includes using the mixed culture, or a supernatant derived therefrom or the purified enzyme itself.

6 Claims, 11 Drawing Figures

METHOD AND THE MICROORGANISM AND ENZYME USED THEREIN FOR DEGRADING THE XANTHAN MOLECULE

BACKGROUND OF THE INVENTION

Xanthan is an anionic extracellular polysaccharide produced by *Xanthomonas campestris* NRRL B-1459. The high viscosity of this polymer solution is relatively insensitive to temperature, ionic strength, shear and pH. For this reason, xanthan finds commercial use as a viscosity-enhancing agent for aqueous solutions. In particular, xanthan is used for enhanced oil recovery. The primary structure of xanthan was established by Jansson et al, 1975, "Structure of extracellular polysaccharide from *Xanthomonas campestris*" Carbohydr. Res. 45, 274–282. It consists of a main chain of β-1,4-linked D-glucose units, as in cellulose, but with a three sugar side chain attached to alternate glucose residues. Pyruvic acetal, i.e., 4,6-0-(1-carboxyethylidene) substituents are on the terminal d-mannosyl residues of some of these side chains. The molecular weight of xanthan varies from $3 \times 10^6$ to $15 \times 10^6$ daltons, depending on the methods and conditions used in the determination of molecular weight.

Xanthan is inert to the attack by microbes or available enzymes, see, e.g., Kelco, Company "Xanthan Gum" Second edition, p. 9, Kelco Co., Clark, N.J. Rinaldo and Milas, 1980, "Enzymic hydrolysis of the bacterial polysaccharide xanthan by cellulase", Int. J. Biol. Macromol. 2, 45–48, were the first to show partial hydrolysis of xanthan by cellulase only in the absence of salt where xanthan is in the unordered conformation. More recently, Cadmus et al (1982) "Biodegradation of xanthan gum by *Bacillus sp*", Appl. Environ. Microbiol., 44, 5–11, reported the biodegradation of xanthan by a Bacillus sp. in the presence of salt. The xanthanase they obtained was a mixture of enzymes that attacked all of the side chain linkages in the xanthan molecule, including the one involving β-1,3-linkage of acetylated mannose to the glucosidic backbone. They found no endo cellulase type of activity in their cultures. Sutherland, (1982), "An enzyme system hydrolyzing the polysaccharides of Xanthomonas species", J. Appl. Bacteriol. 53, 385–393, described an enzyme system hydrolyzing the polysaccharides of Xanthomonas species. The β-glucanohydrolase hydrolyzed both β-1,3- and β-1,4-linked polymers with side-chains or other substituents. Both Cadmus et al and Sutherland deal with mixed cultures to obtain the best activity to degrade xanthan.

In recent enhanced oil recovery field test with xanthan as the viscosity controlling agent, xanthan was found to be degraded by microbial (enzymic) activity. Since then, the biodegradation of xanthan and methods for its prevention have become important research areas. Partial degradation of xanthan into polymers with different molecular weights is also important for more precise investigation of xanthan conformational properties.

The present invention includes a method for degrading the xanthan molecule using a mixed culture, which utilizes xanthan as its carbon source in the presence of salt. The invention also includes the extracellular enzyme(s) produced by the culture which degrade the xanthan molecule. In addition, the invention includes a novel depolymerase which breaks the endo β-1,4-glucosidic linkage of xanthan molecules.

SUMMARY OF THE INVENTION

The present invention includes a method for degrading xanthan molecules. The method includes the steps of contacting the xanthan molecule with a mixed culture including (1) a first soil bacterium, Bacillus sp., obtained from a culture bearing the Agricultural Research Service (ARS) Culture Collection Accession No. NRRL B-15992 and (2) at least one other soil bacterium capable of enhancing the growth of the first soil bacterium when in mixed culture therewith on a xanthan-containing medium, wherein the contacting is conducted under aerobic conditions suitable for the growth of the first soil bacterium and for the elaboration of xanthan-degrading enzymes by the first soil bacterium.

The invention also includes the method for producing a cell-free supernatant which includes a salt-tolerant xanthan depolymerase. The steps of the method include (a) culturing on a xanthan molecule-containing medium a mixed culture comprising (1) a first soil bacterium, Bacillus sp. obtained from a culture bearing the ARS Culture Collection Accession No. NRRL B-15992, and (2) at least one other soil bacterium capable of enhancing the growth of the first soil bacterium when in mixed culture therewith on a xanthan-containing medium; wherein the culturing is conducted under aerobic conditions suitable for the growth of the first soil bacterium and for the elaboration of xanthan depolymerase by the first soil bacterium; and (b) recovering the cell-free supernatant which includes a xanthan depolymerase from the medium, the xanthan depolymerase capable of breaking the endo β-1,4-glucosidic linkage of the xanthan molecule.

Another embodiment of the present invention includes a method for producing a salt-tolerant xanthan depolymerase. The method includes the steps of (a) culturing on a xanthan molecule-containing medium a mixed culture comprising (1) a first soil bacterium, Bacillus sp. obtained from a culture bearing the ARS Culture Collection Accession No. NRRL B-15992, and (2) at least one other soil bacterium capable of enhancing the growth of the first soil bacterium when in mixed culture therewith on a xanthan-containing medium; wherein the culturing is conducted under aerobic conditions suitable for the growth of the first soil bacterium and for the elaboration of xanthan depolymerase by the first soil bacterium; and (b) recovering the supernatant which includes a xanthan depolymerase from the medium, the xanthan depolymerase capable of breaking the endo β-1,4-glucosidic linkage of the xanthan molecule, and (c) recovering the xanthan depolymerase from the supernatant.

The present invention also includes the culture bearing the ARS Culture Collection Accession No. NRRL B-15992, the Bacillus sp., and mutants thereof, and the supernatant obtained therefrom.

DESCRIPTION OF THE PREFERRED EMBODIMENT

Figure 1:
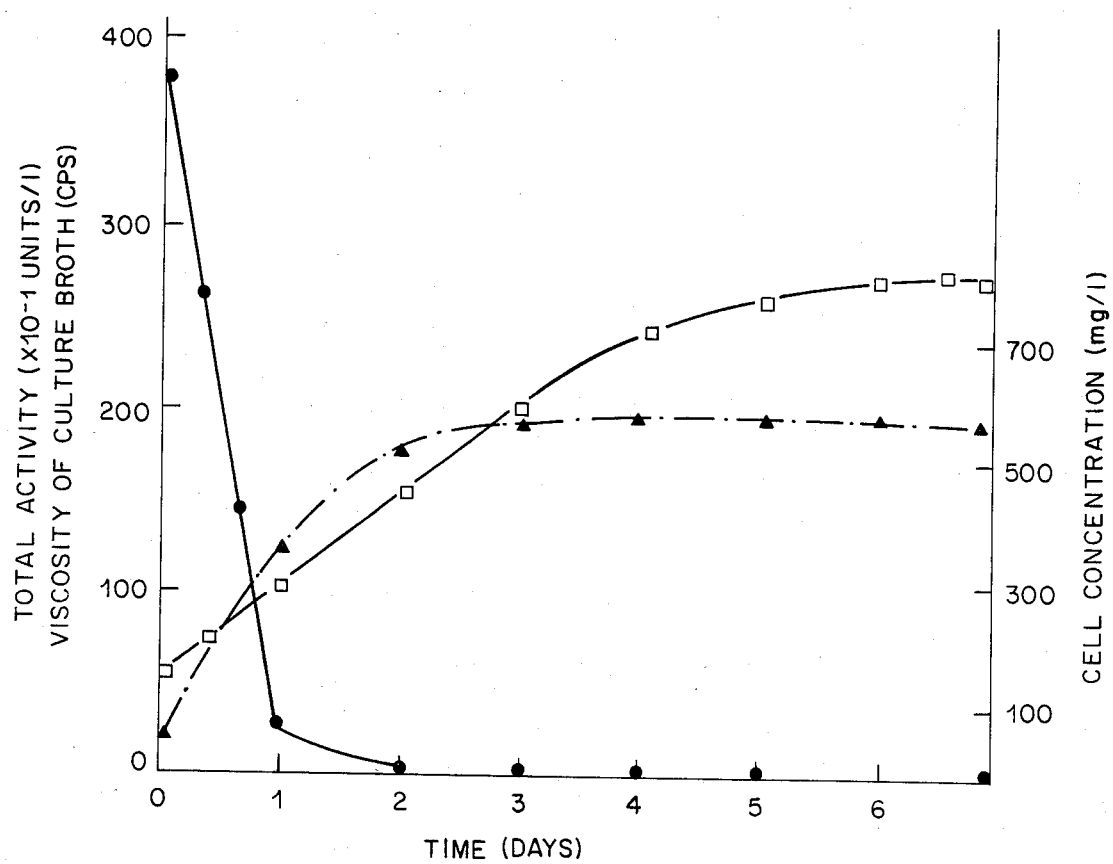
FIG. 1 shows the time course of degradation of xanthan by culture NRRL B-15992. The culture was innoculated into nutrient medium which contained 2% NaCl and xanthan at 30° C. At each time interval, samples were taken and assayed for cell yield, solution viscosity, and enzyme activity. Cell yield (-----) was measured at 660 nm. Solution viscosity (—) was measured at 25° C. Enzyme activity (□-□-□) was determined by measuring reducing sugar groups released per minute using fresh xanthan stock solution.

A salt-tolerant xanthan-utilizing mixed culture was isolated from a soil sample of Linden, N.J. The culture was maintained on a 2% salt-containing nutrient agar which contained glucose, mannose, and xanthan as the carbon and energy sources. For the production of xanthan degrading enzymes, the culture was grown at 30° C. aerobically in a 2.8 liter shake flask containing one liter of medium with the following composition (per liter): 2.5 g xanthan, 0.5 g of $(NH_4)_2SO_4$, 0.8 g of yeast extract, 0.4 g peptone, 1.5 g of $KH_2PO_4$, 0.7 g of $K_2HPO_4$, 2.0 g $NaNO_3$, 20 g NaCl and 10 ml trace metals solution. The composition of the trace metals solution was (per liter): 0.5 mg $CuSO_4.5H_2O$, 1 mg $H_3BO_3$, 0.7 mg $MnSO_4.H_2O$, 10 mg $ZnSO_4.7H_2O$, and 1 mg $MoO_3$. Xanthan-degrading cultures were grown in Erlenmeyer flasks (300 ml) containing 50 ml of medium, or Fernbach flasks (2.8 liter) containing 1 liter of medium. These flasks were innoculated with a 3-day-old innoculum (1% v/v) that had been grown in an Erlenmeyer flask innoculated with a loopful of culture. All flasks were shaken at 200 rpm on a rotary shaker at 30° C.

The microorganisms were screened for xanthan-degrading activity by innoculating a soil (1 g) or water sample (1 ml) into liquid nutrient medium containing 1560 ppm xanthan and 4% NaCl (initial solution viscosity 240 cps) for screening xanthan-degrading aerobic microorganisms. The reduction in viscosity of culture broth was used as indication of xanthan-degrading activity. These xanthan degrading activities could be enhanced by several transfers of the cultures.

Viscosities were measured at 25° C. with a viscosimeter such as a Contraves low shear 30 at a shear rate of 1.3 sec.$^{-1}$. In a cell-free system, the activity measurements for releasing reducing sugar groups were conducted by incubating 2.5 ml of xanthan stock solution and a small amount of enzyme(s) at 25° C. Xanthan stock solution was prepared by dissolving 0.188% xanthan, 0.4 mM $MgSO_4$ and 0.03 mM $MnSO_4$ in 0.05 M sodium acetate buffer pH 5.4. At certain time intervals, samples were taken for reducing sugar assay. Reducing sugars, calculated as glucose, were determined by the method of Somogyi, M., (1945), "A New Reagent for the Determination of Sugars", *J. Biol. Chem.*, 160, 61–69. One unit of enzyme activity was expressed as one μmole reducing sugar group released (as glucose) per minute.

The inoculum, about 2%, was a 3-day-old shake flask culture of the same medium. The flasks were shaken at 200 rpm at 30° C. Xanthan-degrading enzyme(s) was harvested after 3 to 4 days of incubation when the maximum yield was reached. The mixed culture is deposited in the ARS Culture Collection under Accession No. NRRL B-15992.

Microscopic examination of the salt-tolerant cultures obtained from the Linden soil sample that degraded xanthan revealed a stable mixture of two species. These two species were separated from each other on a solid medium. They are: a motile, slow-growing, spore-forming short rod, forming yellow colonies on agar plates; and a short fan non-motile rod, forming mucoid colonies on agar plates. These two species were difficult to separate from each other due to the relative slow growth rate of the Bacillus and the apparent affinity in proximity to each other for growth on agar plate. The motile gram positive, catalase positive spore-forming short rod, a Bacillus, was identified as the one that degraded xanthan (judging from viscosity reduction: 50% viscosity reduction in one week). However, the presence of the other species (identified as Flavobacterium sp.) stimulated the xanthan-degrading activity. The stable mixed culture is hereinafter designated NRRL B-15992. The growth of culture B-15992 was not inhibited by up to 5% salt (NaCl) concentration. However, cell growth was somewhat slower in salt concentration between 6–8%. At 10% salt concentration, the growth of culture NRRL B-15992 was completely inhibited. The salt tolerant cultures obtained from two other locations which degrade xanthan were also mixed cultures containing short fat and/or thin rods both motile and non-motile, and cocci.

The xanthan degrading activity by the Bacillus obtained from B-15992 with be increased by the presence of any other microorganism or combination of microorganisms which enhances the growth of the Bacillus when in mixed culture therewith on a suitable xanthan-containing medium. This includes most species of soil genera. Illustrative thereof, without limitation thereto, are Arthrobacter, Alcaligenes, Agrobacterium, Bacillus, Brevibacterium, Alavobacterium, Micrococcus, and Xanthomonas. The same is true of the Flavobacterium sp. obtained from B-15992. The enhanced enzyme production in mixed culture is indicative of a commensalistic or symbiotic relationship accruing to the benefit of the xanthan depolymerase producer.

Biodegradation of Xanthan by Mixture Culture

The time course of xanthan degradation activity of B-15992 was followed by measuring the amount of reducing sugar released per minute using a fresh xanthan stock solution. Results are shown in FIG. 1. The cell growth reached its stationary phase in about 3 days. Viscosity of the culture broth decreased from 400 cps to about 30 cps within 24 hours. Xanthan-degrading activity, as measured by reducing sugar assay, continued to increase during the first 4 days of incubation. Culture B-15992 evidentally can break the xanthan molecule to monosaccharides.

The effect of temperature and pH on growth and on xanthan-degrading activity of culture B-15992 were studied at temperatures from 4° to 60° C. and pH from 3.0 to 9.0.

Two criteria were followed: cell growth, and the changes in viscosity of culture broth which represented xanthan-degrading activity. Assay was conducted after two days of incubation. The optimum temperature for cell growth was about 30°–35° C. The viscosity of the culture broth was almost completely lost when the culture was incubated for 2 days at a temperature between 25° and 40° C. Culture B-15992 could not grow at a temperature higher than 50° C. or below 10° C., and therefore no viscosity reduction was observed at these temperatures. Optimum pH for growth of B-15992 at 30° C. was found to be between 5 and 7. At pH below 4 or above 8, there was very little growth of culture B-15992, and therefore, the viscosity reduction was not significant. Based on solution viscosity measurement, pH 6 was the optimum for xanthan-degrading activity during cell growth.

Biodegradation of Xanthan by Culture Supernatant

Figure 2:
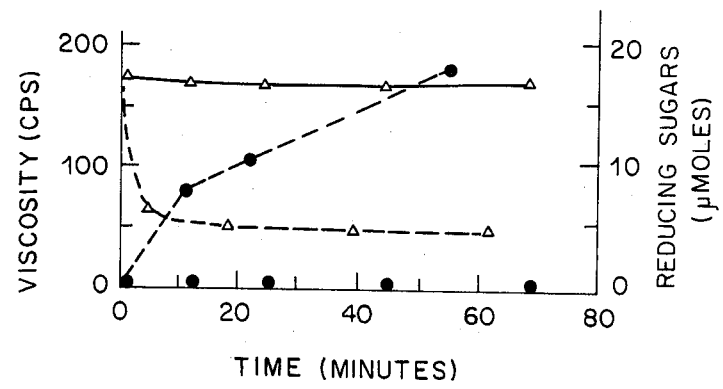
FIG. 2 shows degradation of xanthan by a cell-free system of culture NRRL B-15992. Three-day-old culture broth of NRRL B-15992 was centrifuged and the cell-free supernatant concentrated and washed 3 times with 0.05 M sodium phosphate buffer pH 7.0 in an ultrafiltration unit with PM 10 membrane. A 1.24 mg protein sample of the cell-free concentrate was incubated with xanthan in 14 ml 0.05 M sodium acetate buffer pH 5.4 at 40° C. At each time interval, samples were taken for reducing sugar (o - -o- -) and viscosity (Δ--Δ--Δ) assays. Solid line control (xanthan solution with washed cells suspension, with disintegrated cells suspension, or without addition).

Experiments show that xanthan-degrading enzyme(s) are located extracellularly. Three-day-old culture broth of culture B-15992 grown on xanthan in the presence of 2% salt was centrifuged to remove cells. The supernatant was concentrated and washed 3 times with 0.05 M phosphate buffer, pH 7.0 in an ultrafiltration unit (Amicon Unit with a PM 10 membrane). The cells were washed twice with a 10 times volume of 0.05 M phosphate buffer, pH 7.0, centrifuged, and were resuspended in a small amount of the same buffer. A portion of this washed cells suspension was disintegrated by two passages through a French pressure cell (American Instruments Co., Silver Springs, Md.) at 20,000 lb/in$^2$. The disintegrated cells suspension and the washed cells suspension were also tested for their xanthan-degrading ability. Neither of these two samples could degrade xanthan. Only the concentrated culture supernatant showed xanthan-degrading activity. As shown in FIG. 2, the sharpest reduction in solution viscosity was found during the initial 5 minutes of incubation. After that, the decrease in solution viscosity became slower. However, the production of reducing sugar groups showed increases during the entire incubation period indicating further cleavage of fragmented xanthan molecules.

In order to determine whether the xanthan-degrading enzyme(s) is constitutive or inducible, culture B-15992 was grown on nutrient medium containing different carbon sources, i.e., glucose, mannose, glucose+mannose, xanthan, cellulose, carboxymethyl cellulose, DEAE cellulose, succinate, pyruvate, starch, cellulose acetate, or without carbon source addition. Cell growth was observed on all of the flasks (OD at 660 nm ranging from 0.7 to 2.17, grown for 2 days at 30° C.). However, only xanthan-containing media produced xanthan-degrading enzyme activity in the cell-free culture broth. Therefore, it is clear that the xanthan-degrading enzyme(s) was induced only in the presence of xanthan.

Figure 3:
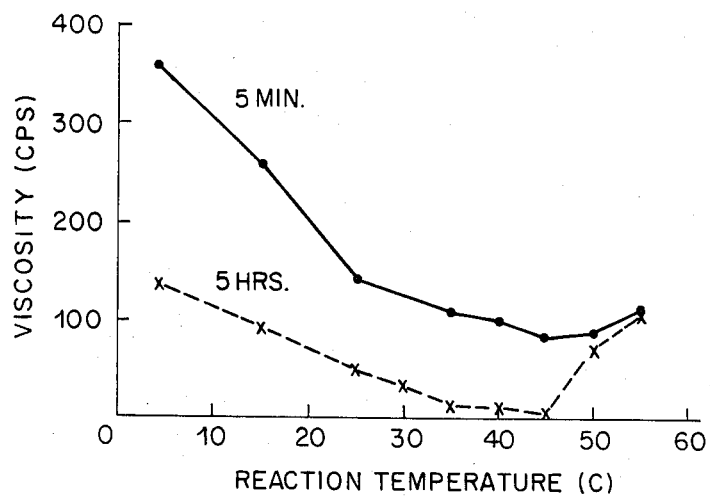
FIG. 3 shows the effect of temperature on the activity of xanthan-degrading enzyme(s). Concentrated and washed crude enzyme fraction obtained from cell-free culture broth of NRRL B-15992 grown at 30° C. for 3 days was used. A 100 l sample of crude enzyme fraction was added into 6 ml of reaction mixture which had been preincubated at the set temperature for 15 minutes. The initial viscosity of the reaction mixture was 410 cps. The reaction was conducted at the temperature indicated for both 5 minutes (solid line) and 5 hours (broken line). The viscosity of the reaction mixture was recorded.

The effect of temperature on the activity of xanthan-degrading enzyme(s) was studied at temperatures ranging from 4° C. to 55° C. by measuring the changes in solution viscosity. A crude enzyme fraction obtained from cell-free culture broth of B-15992 grown at 30° C. for 4 days was used for this study. The remaining viscosity of the reaction mixture was recorded at both 5 minutes and 5 hours of incubation at the indicated temperature. Results are shown in FIG. 3. It is clear that the optimum temperature for the activity of xanthan-degrading enzyme(s) is between 35°–45° C. The enzyme(s) degraded xanthan slowly at 4° C. and was not stable at a temperature higher than 50° C.

On storage, the crude enzymes were stable at 4° C. for at least 6 months.

Figure 4:
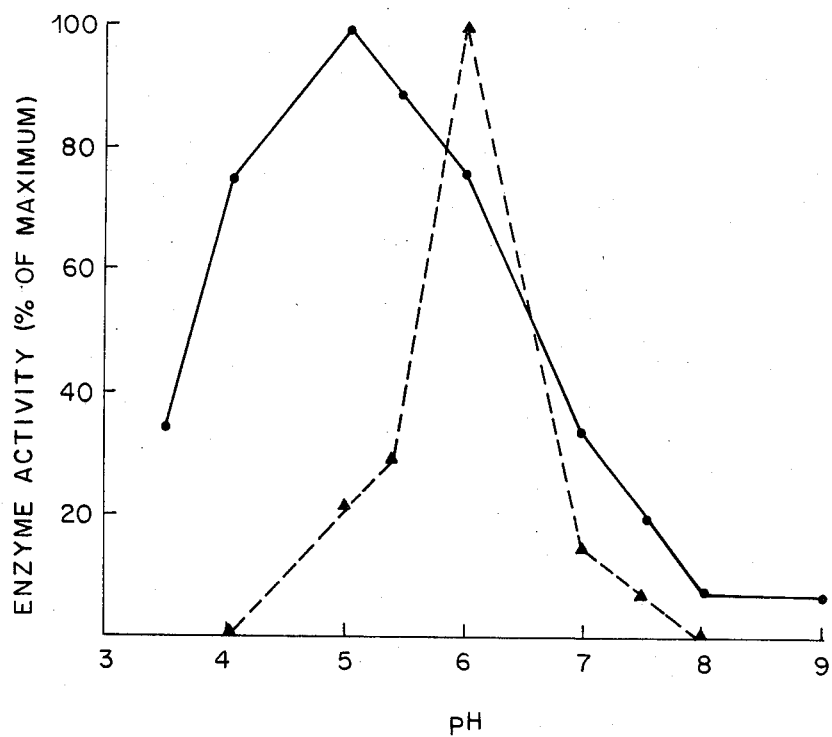
FIG. 4 shows the effect of pH on the activity of xanthan-degrading enzyme(s). The same crude enzyme fraction as for FIG. 3 was used. Various buffer solutions (0.05 M) are described in the text. Enzyme activities are expressed as % of maximum for viscosity reduction (solid line) and for release of reducing sugar groups (broken line).

In order to determine the effect of pH on the activity of xanthan-degrading enzyme(s), xanthan was dissolved in different buffer solutions (0.05 M) at various pH values: sodium acetate buffer for pH 3.5 to 6.0; sodium phosphate buffer for pH 6.0 to 7.5; and tris (hydroxymethyl) aminomethane buffer for pH 8.0 to 9.0. Enzyme activity was followed by both the decrease in solution viscosity and the production of reducing sugar groups. Results are shown in FIG. 4. In the cell-free system, the optimum pH for reducing solution viscosity and for producing reducing sugar groups appears to be about 5.0 and 6.0, respectively. This indicates that these two reactions are possibly carried out by different enzymes. Xanthan solution itself without the addition of crude enzymes showed no changes in viscosity and reducing sugar groups at the pH values tested.

The degradation of xanthan by concentrated cell-free supernatant was conducted at 40° C., pH 6 buffer solution for 18 hours. In order to study the products of the degradation, the reaction mixture was filtered through an ultrafiltration unit (Amicon Unit using a PM 10 membrane to separate a low molecular weight fraction, LMWF, less than 10,000 daltons molecular weight) and a high molecular weight fraction (HMWF). The LMWF was concentrated with a rotary evaporator and was de-salted with a Bio-Gel P-2 column. The de-salted LMWF was again concentrated and analyzed on thin-layer chromatography plates for monosaccharides. The solvent system was pyridine-ethyl acetate-acetic acid-water (5:5:1:3 v/v). Sugars on t.l.c. plates were detected by spraying the plates with p-anisidine-phthalic acid reagent. Acetylated hexose was determined qualitatively by spraying Hestrin reagent on the plate. For determination of pyruvic acid, the area corresponding to pyruvated mannose was collected from t.l.c. plates and was eluted with distilled water. The aqueous solution was centrifuged to remove debris and dried by vacuum evaporation. The presence of pyruvic acid was determined by the enzymatic method of Duckworth and Yaphe, (1970), "Definitive Assay for Pyruvic Acid in Agar and Other Algal Polysaccharides", *Chem. Ind.* (London) 23, 747-748. Results obtained show that all of the components of xanthan, i.e., glucuronic acid, pyruvated mannose, glucose, mannose and acetylated mannose were detected in the LMWF. These were different from xanthanase (see Cadmus, U.S. 4,410,625) which attacked all of the side chain linkages without breaking the glucosidic backbone of xanthane.

The distribution of total carbohydrate and reducing sugar groups produced in LMWF and HMWF were studied. Results are listed in Table 1. After 18 hours incubation in the presence of the crude enzyme(s), almost all of the reducing sugar groups and total carbohydrate were found in the LMWF. The remaining carbohydrate in the HMWF was only 13%.

TABLE 1

Distribution of Total Carbohydrate and Reducing Sugar in Different Molecular Weight Fractions Produced From Xanthan by Cell-Free Culture Broth of Culture B-15992

| | LMWF | | HMWF | |
|---|---|---|---|---|
| time (hr) | R. sugar (g/5 ml) | Total $CH_2O$ (%) | R. sugar (g/5 ml) | Total $CH_2O$ (%) |
| 0 | 0.330 | 30 | 0.090 | 70 |
| 18 | 106.13 | 87 | 0.124 | 13 |

Figure 5:
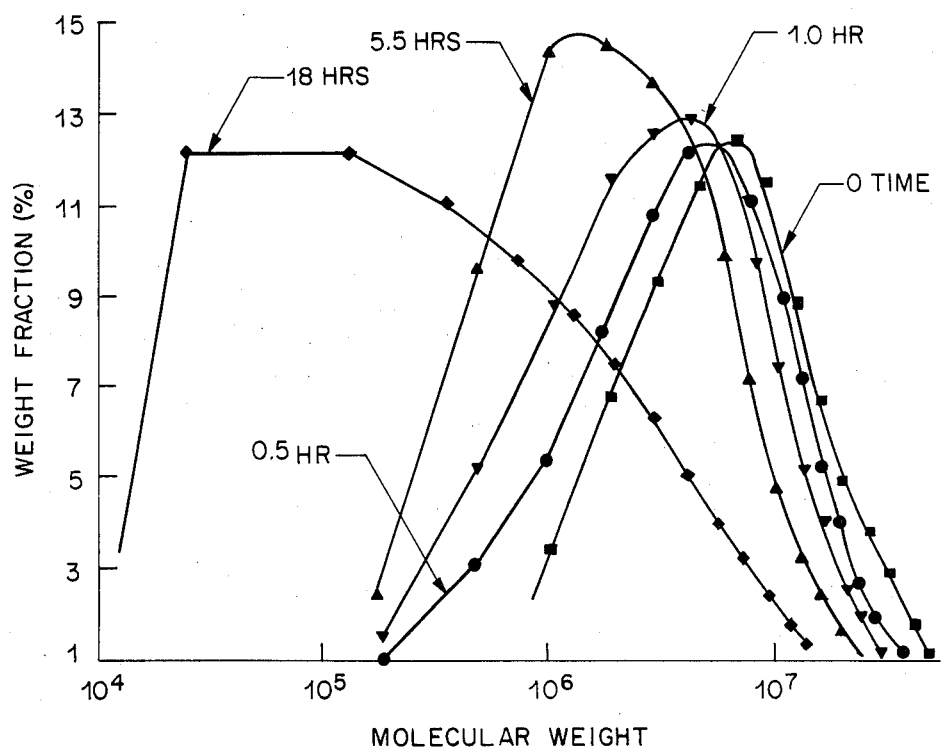
FIG. 5 shows the molecular weight distribution shifts of xanthan samples (HMWF). Cell-free enzyme preparation (10 mg protein) was incubated with 144 mg xanthan in 80 ml 0.05 M sodium acetate buffer, pH 6.0 at 40° C. Samples were taken at indicated time and were boiled for 5 minutes to deactivate the enzymes. The HMWF of the reaction products was subjected to molecular weight distribution studies by using the fluorescent derivative method.

The HMWF was assayed for its molecular weight distribution. Flourescent derivatives of xanthan were prepared by isocyanide coupling of fluoresceinamine to the carboxy groups of xanthan. A method developed by Holzwarth, G., (1978) "Molecular weight of xanthan polysaccharide", *Carbohydrate Research*, 66, 173-186, was followed for the molecular weight distribution studies. The weight average molecular weight of xanthan decreased from $6.5 \times 10^6$ to $6.0 \times 10^4$ in 18 hours of incubation in the presence of the cell-free enzyme preparation (see FIG. 5).

Chemicals and biocides, including those used in enhanced oil recovery operations were studied for their effect on the growth of culture B-15992 and on the activity of xanthan-degrading enzyme(s). Both aerobic and anaerobic conditions were tested. In order to simulate the conditions used in EOR field operation, xanthan was produced in the laboratory by growing *Xanthomonas campestris* according to the published procedure, Jeanes, A., et al, (1976), "Polysaccharide (xanthan) of *Xanthomonas campestris* NRRL B-1459: Procedures for culture maintenance and polysaccharide production, purification and analysis". Agricultural Research Service, U.S. Department of Agriculture AR-NC-51. After centrifugation, the culture broth was autoclaved and was diluted with brine to about 300 cps viscosity. A cell suspension of culture B-15992 obtained from colonies grown on agar plates was used as the innoculum. Growth of B-15992 was followed by monitoring decreases of viscosity of the culture broth and by microscopic observation. Results are listed in Table 2. The presence of 10 ppm of a biocide, DBNPA, was not effective in preventing the growth of B-15992. The solution viscosity was lost within 5 days of incubation. Twenty five ppm of formaldehyde was somewhat more effective; it took 9 days for B-15992 to degrade the xanthan solution. In the presence of 50 ppm formaldehyde, no changes in solution viscosity or cell growth was observed during 30 days of incubation. A combination of sodium dithionite, formaldehyde, and DBNPA at concentrations similar to those used in EOR operation slowed cell growth and solution viscosity loss over nine days. Under anaerobic conditions, there was no growth of B-15992 and no loss in solution viscosity either in the presence or absence of these chemicals.

TABLE 2

Effect of Chemicals and Biocide on Growth of Culture B-15992

| | | Viscosity (cps after days incubation) | |
|---|---|---|---|
| Compounds | Concentration | Aerobic | Anaerobic |
| control | — | 1.0 | 300 |
| $Na_2S_2O_4$ | 75 ppm | 1.0 | 300 |
| HCHO | 25 ppm | 1.5 (9 days) | 300 |
| | 50 ppm | 300 | 300 |
| DBNPA | 10 ppm | 1.5 (5 days) | 300 |
| $Na_2S_2O_4$ + HCHO + DBNPA | (75 ppm + 25 pm + 10 ppm) | 1.5 (9 days) | 300 |
| Triton X-100 | 500 ppm | 90 | 300 |

TABLE 2-continued

| Effect of Chemicals and Biocide on Growth of Culture B-15992 | | Viscosity (cps after days incubation) | |
|---|---|---|---|
| Compounds | Concentration | Aerobic | Anaerobic |
| polypropylene glycol | 500 ppm | 120 | 300 |

The above experiments were repeated using cell-free enzyme preparations obtained from culture broth of B-15992 grown on xanthan for 3 days. A concentrated crude enzyme fraction was incubated with the individual chemicals or a combination of these chemicals either in the presence or absence of air. The results obtained showed that none of these chemicals at the concentrations indicated (same as table 2), tested individually or in combination, in either anaerobic or aerobic conditions, inhibited the activity of the xanthan-degrading enzyme(s). The solution viscosities in all cases (except those control tests which contained no enzyme(s)) were lowered markedly within the first couple of hours of incubation. These data indicate that the presence of a small quantity of this enzyme(s) could cause problems in an EOR operation that uses xanthan as a solution viscosity enhancing agent.

Biodegradation of Xanthan by Xanthan Depolymerase

A novel xanthan depolymerase was purified from the culture supernatant and examined for its effect on degrading xanthan. In the following, enzyme assays were conducted with either viscosity or reducing sugar measurements by incubating a 1.25 ml xanthan stock solution and a small amount of enzyme(s) at 25° C. Xanthan stock solution was prepared by dissolving 0.188% xanthan, 0.4 mM $MgSO_4$, and 0.03 mM $MnSO_4$ in 0.05 M sodium acetate buffer pH 5.4. At certain time intervals samples were taken for either viscosity or reducing sugar assay. Viscosity was measured at 25° C. (using a Contraves low-shear 30 rheometer, Middlesex, U.K. at a shear rate of 1.3 $sec.^{-1}$). The rheometer was equipped with a refrigerated circulating bath (Neslab Endoccal bath, Portsmouth, N.H.). Reducing sugars, calculated as glucose, were determined by the method of Somogyi, M., (1945), "A New Reagent for the Determination of Sugars", J. Biol. Chem. 160, 61–69. Initial tests on time profile studies of these assay methods using concentrated cell-free broth of culture B-15992 showed that both reactions took place immediately. The changes in viscosity and reducing sugars between two time intervals (1.0 min to 2.0 min for Δ cps, 0.5 min to 1.5 min for Δ reducing sugars) were measured. Enzyme activity (in units) was expressed as Δ cps/min (depolymerase) or Δμmoles reducing sugar group released (as glucose) per min. (for both endo and exoglucanases). Specific enzyme activity was expressed as units per mg of protein.

α-Mannosidase (or β-mannosidase) activity was assayed by incubating 0.25 ml 0.1 M citrate buffer pH 4.5, 0.25 ml 0.01 M p-nitrophenyl-, D-mannopyranoside (or p-nitrophenyl-βD-mannopyranoside) and 50 μl of enzyme solution at 25° C. for 5 minutes. After the reaction, 2 ml 0.2 M borate buffer pH 9.8 was added to stop the reaction. The amount of nitrophenyl liberated was measured at 405 nm and calculated using the molar extinction coefficient for nitrophenyl $18.5 \times 10^3$.

The purification of the enzyme was obtained by the method described below. All steps were performed at 4° C. Unless otherwise state, the buffer solution was 0.05 M sodium phosphate buffer, pH 7.0.

The steps include the use of a number of commercially available units to aid in the purification of the enzyme such as ion exchange columns and molecular sieves. However, it is understood that other commercially available units may be used to perform the chromatography.

1. Step 1 Ultrafiltration concentration

After 3 days of growing culture B-15992 on xanthan at 30° C., cells were removed by centrifugation at 10,000 xg for 20 minutes. The cell-free supernatant (30 liters, collected from several batches) was concentrated in an ultrafiltration unit (Amicon Model DC-10 with Hollow fiber H10P10-20 cartridge to 500 ml, 10,000 molecular weight cutoff). It was then washed with 0.05 M phosphate buffer pH 7.0 with three replacements of volume.

2. Step 2 DEAE-cellulose column chromatography

Figure 6:
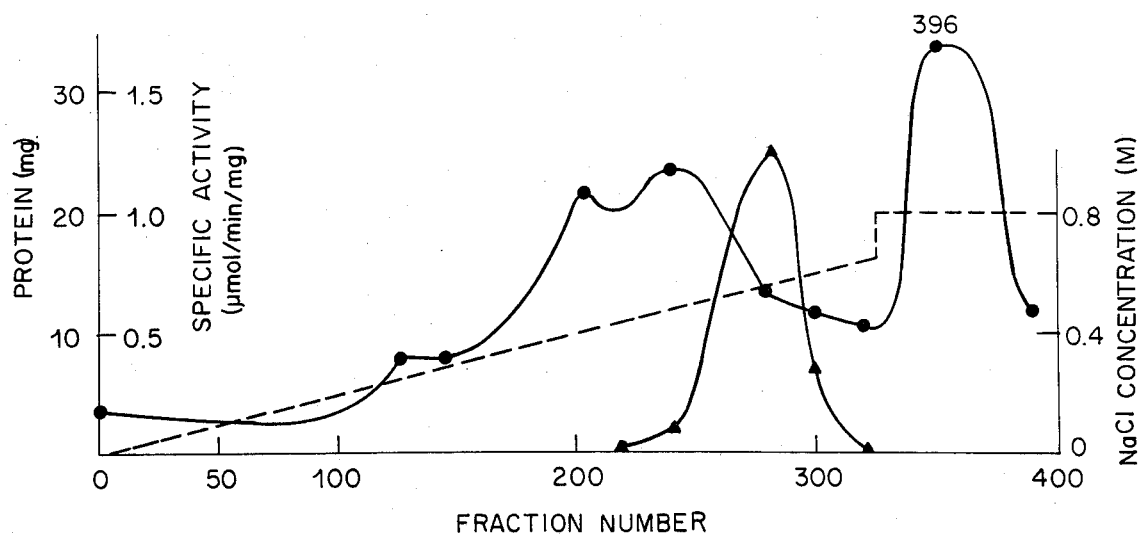
FIG. 6 shows the DEAE-cellulose column chromatography of xanthan-degrading enzyme(s) from culture broth of NRRL B-15992. Concentrated cell-free culture broth of NRRL B-15992 grown on xanthan was applied. Twenty-milliliter fractions were collected. Symbols: o - o, protein; Δ-Δ, specific enzyme activity by reducing sugar assay; - - - -, NaCl concentration.

The concentrated and washed fraction from step 1 was applied to a DEAE-cellulose column which had been equilibrated with 0.05 M sodium phosphate buffer pH 7.0. The column (10.5 cm diameter, 33 cm long) was washed with 3 liters of the same buffer, and then was eluted by a linear gradient of 0 to 0.6 M NaCl in the same buffer. Final elution of the column was carried out with the same buffer containing 0.8 M NaCl. Each 20-ml fraction was collected. As is shown in FIG. 6, gradient fraction numbers 225–320 contained enzyme activities for xanthan degradation (both reducing sugar production and viscosity reduction). Very small amounts of α- and β-mannosidase activities were found in the wash fraction (specific activities in n moles/min/mg were 0.42 for α-mannosidase and 0.44 for β-mannosidase). Fractions 225–320 were combined, concentrated and washed with 0.05 M phosphate buffer pH 7.0 (using an Amicon hollow fiber concentration Model DC 2 with HP-10-20 cartridge, 10,000 molecular weight cutoff).

3. Step 3 DEAE-Biogel Column Chromatography

Figure 7:
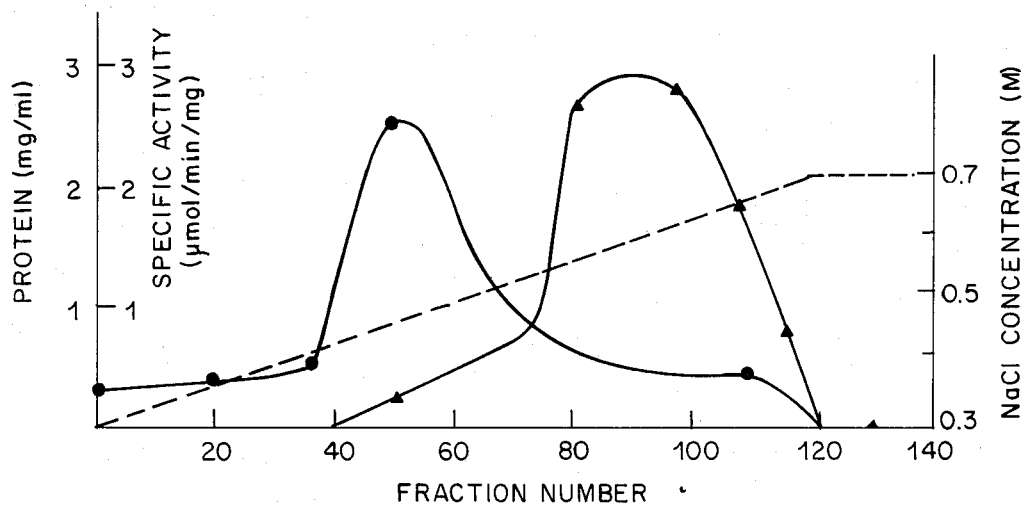
FIG. 7 shows the DEAE-BioGel column chromatography of xanthan-degrading enzyme(s). Enzyme fraction obtained from step 2 was used. Fifteen milliliter fractions were collected. Symbols: o--o, protein, Δ--Δ, specific enzyme activity by reducing sugar assay, ----, NaCl concentration.

The concentrated fraction (190 ml) obtained from step 2 was applied to a DEAE-Biogel column (5.6 cm$\phi$×27 cm) which had been equilibrated with 0.05 M sodium phosphate buffer, pH 7.0. The column was washed with 1 liter of the same buffer containing 0.3 M NaCl. It was then eluted with a linear gradient of one liter each of 0.3 M and 0.7 M NaCl in the same buffer. Each 15 ml fraction was collected. FIG. 7 shows the NaCl gradient elution of the DEAE-Biogel column chromatography. Fractions 75 to 115 showed high enzyme activity assayed by the production of reducing sugars. These same fractions also had the ability to decrease viscosity of xanthan solutions. These fractions were combined and concentrated in an ultrafiltration unit (Amicon unit with a PM 10 membrane).

Step 4. High performance liquid chromatography

High performance liquid chromatography (HPLC) was performed with a Varian Model 5000 HPLC (Florham Park, N.J.) which had been equipped with a Varian refractive index detector RI-3 and/or a Perkin Elmer LC 75 UV detector, (Norwalk, Conn.). Protein separation was performed using a Synchropak AX 300 column obtained from Varian Associates, Inc. Monosaccharide and oligosaccharide analyses were performed, respectively, using two types of columns obtained from Bio-Rad Laboratories, Aminex HPX-87C and Aminex HPX-42A. HPLC analyses of carbohydrates were performed at 85° C.

Figure 8:
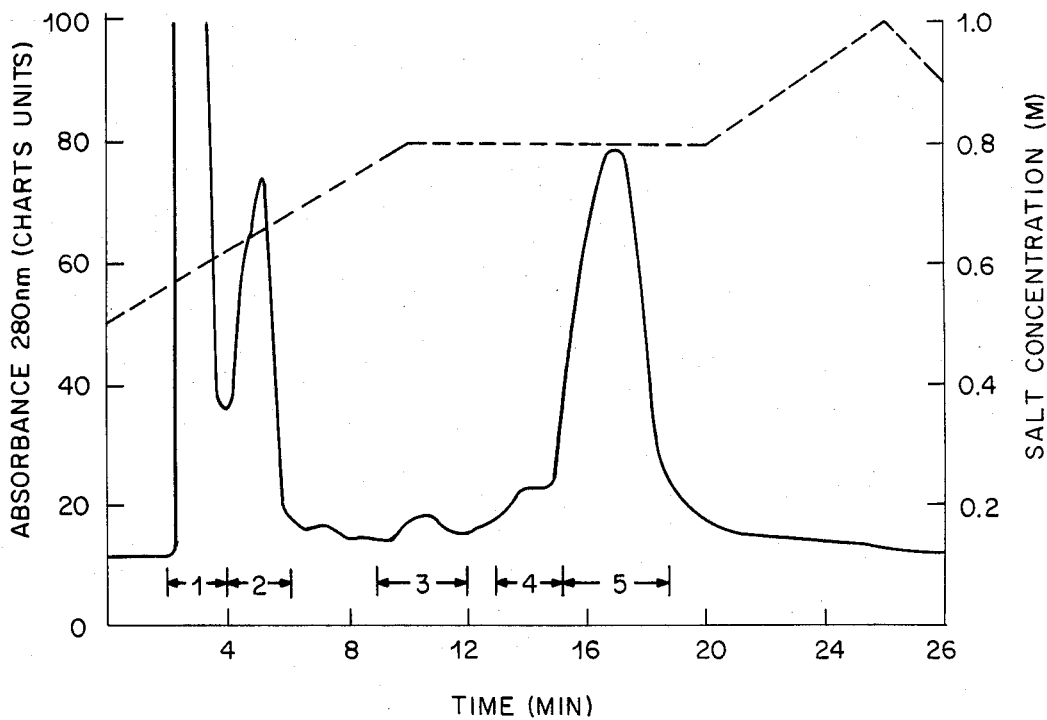
FIG. 8 shows the high pressure liquid chomatography of xanthan-degrading enzyme. Enzyme fraction obtained from step 3 was used. A 0.5 ml sample was applied in each run. Symbols: —, absorbance at 280 nm; ------, salt concentration.
Figure 9:
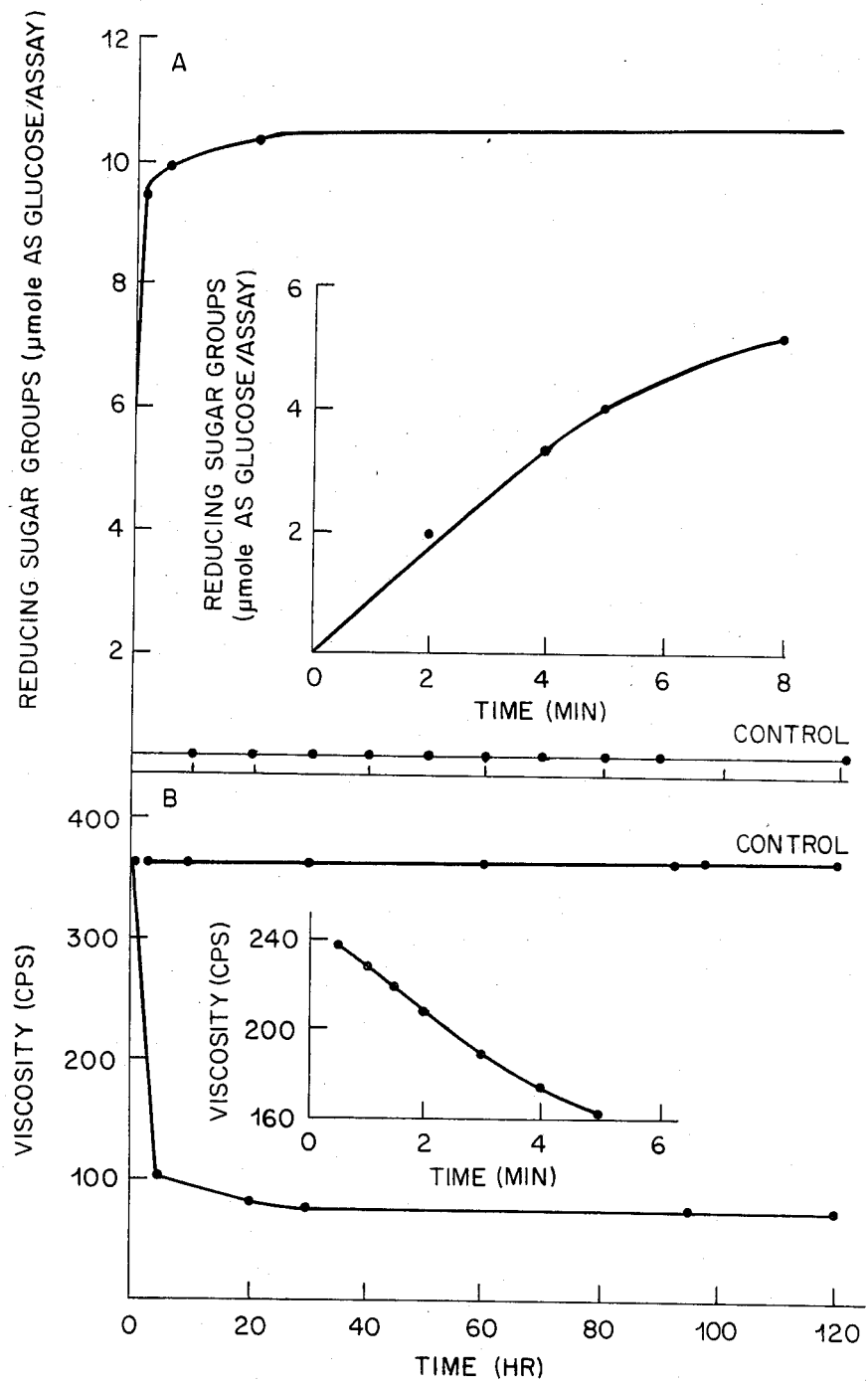
FIG. 9 shows the time course of degradation of xanthan by purified enzyme fraction from step 4 purification. The reactions were conducted as described in the text. Enzyme activity assays were followed by both the release of reducing sugar groups (FIG. 10A) and the decrease in solution viscosity (FIG. 10B). Controls had no addition of enzyme fraction. Inserts were data obtained from experiments of shorter incubation time. The viscosity assays for the inserts of FIG. 10B were conducted at 25° C. in the measuring cup of contraves rheometer.

The concentrated fraction obtained from step 3 was applied to an HPLC with the Synchropak AX 300 column. The mobile phase was 0.05 M sodium phosphate buffer pH 7.0. The column was eluted with a programmed pattern of NaCl gradient. FIG. 8 shows protein patterns separated by HPLC. Each protein peak was collected. Their enzyme activities were tested. Both the activities for viscosity reduction and for release of reducing sugar groups were found in protein peak #5 of the HPLC separation. Several runs were performed to collect sufficient amount of protein peak #5 fraction for the following studies. A summary of enzyme purification is listed in table 3. A 55 fold purification was achieved.

as measured by viscosity and reducing sugar assays. Time profile studies of xanthan degradation by the purified enzyme fraction are shown in FIG. 9. Enzyme activity was followed by both release of reducing sugar groups (FIG. 9A) and solution viscosity changes (FIG. 9B). The release of reducing sugar groups was linear for the first five minutes and tapered off after that. A similar reaction pattern was observed in the viscosity assay. Therefore, enzyme activity was measured during the initial 3 minutes of reaction for either reducing sugar assay or viscosity assay. At 20 hours of incubation, an additional amount of enzyme was added to the reaction mixture. No further release of reducing sugars or further decrease in solution viscosity was observed.

Degradation products of xanthan formed by the enzyme fraction from purification step 4 were separated and studied. Enzyme 2.5 mg protein was incubated with 144 mg xanthan in 80 ml 0.05 M sodium acetate buffer pH 5.4 at 35° C. At certain time intervals, samples were taken and were boiled for 5 minutes to deactivate the enzyme. Samples were then separated into low molecular weight fraction (LMWF) and high molecular

TABLE III

Purification of Xanthan-depolymerase from Xanthan-Grown Culture B-15992

| | | Enzyme Activity | | | | | |
|---|---|---|---|---|---|---|---|
| | | Reducing sugar assay | | | Viscosity assay | | |
| Steps | Total Protein (mg) | Specific Activity *2 | Total Units *1 | Recovery (%) | Specific Activity *4 | Total Units *3 | Recovery (%) |
| 1. Concentrated cell-free broth | 4858 | 1.6 | 7772 | 100 | 12.2 | 59,267 | 100 |
| 2. DEAE-cellulose column chromatography | 603 | 2.0 | 1206 | 15.5 | 10.2 | 6,150 | 10.4 |
| 3. DEAE-Biogel column chromatography | 30 | 19. | 570 | 7.3 | 168.6 | 5,058 | 8.5 |
| 4. HPLC | 7 | 77. | 540 | 6.9 | 657 | 4,599 | 7.7 |

Notes:
*1. One unit is expressed as one μm mole reducing sugar (caculated as glucose) produced per minute
*2. Specific activity is expressed as units per mg protein.
*3. One unit is expressed as a change in viscosity of one cp per minute.
*4. Specific activity is expressed in units per mg protein.

Acrylamide gel electrophoresis was conducted in 10% gel. Gels were stained with Coomassie brilliant blue. Sodium dodecyl sulfate electrophoresis was carried out in a 12% polyacrylamide gel according to the method of Weber and Osborn. The enzyme solution was preincubated for 3 min at 100° C. in a small amount of 100 mM sodium phosphate buffer, pH 7.0 containing 1% sodium dodecyl sulfate. The marker proteins used were: soybean trypsin inhibitor (19,900), carbonic anhydrase (28,800), ovalbumin (42,600), bovine serum albumin (67,600), phosphorylase B (95,500), and β-galactosidase (131,800).

The purity and molecular weight of the enzyme was determined. The purified enzyme fraction obtained from step 4 HPLC exhibited a single protein band in polyacrylamide gel electrophoresis. The molecular weight of the xanthan depolymerase estimated by a calibrated Bio-Gel A-0.5 m column was 60,000 daltons. Electrophoresis in a 12% polyacrylamide gel in the presence of sodium dodecyl sulfate also gave a single-protein band with a molecular weight of 60,000 daltons indicating that the enzyme consisted of a single sub-unit. Attempts to apply a glycoprotein stain to the enzyme on polyacrylamide gel showed that this enzyme contained no sugar moiety.

The time profile of the xanthan depolymerase activity was monitored. Control experiments with either heat-killed or no enzyme showed no degradation of xanthan weight fraction (HMWF) by passing through an Amicon ultrafiltration unit with PM 10 membrane (10,000 molecular weight cut-off). The LMWF was concentrated with a rotary evaporator and was desalted with a Bio-Gel P-2 column. The de-salted LMWF was again concentrated and was either assayed for total carbohydrate content by the phenol-sulfuric acid method or analyzed for monosaccharide by thin layer chromatography. The HMWF was subjected to molecular weight distribution studies using the fluorescent derivative method described previously.

The reaction products of the enzymatic activity were identified. The reaction products at 0, 0.5, 1, 5.5, and 18 hours of incubation were studied. Thin layer chromatography assay of these LMWF showed that there was no monosaccharide produced from xanthan by the action of xanthan depolymerase. This was confirmed by monosaccharide analyses (using Aminex HPX-87C column with HPLC). The oligosaccharide in LMWF was further assayed with HPLC (using an Aminex HPX-42A column). A peak detected on this column gave molecular weight of the oligosaccharide at greater than DP15 (15 monosaccharide units, the upper limit of resolution for this HPLC column). The oligosaccharide(s) (smaller than 10 pentasaccharide units or 10,000 molecular weight) in LMWF was not further identified. Total carbohydrate in these LMW fractions was less than 5% of the substrate xanthan. The HMWF of 0.5 hr sample was assayed for its molecular weight distribution by using the fluorescent derivative method. The weight average molecular weight of xanthan decreased from 6.5 to $10^6$ daltons to $8.0 \times 10^5$ daltons by the action of the purified enzyme fraction.

Figure 10:
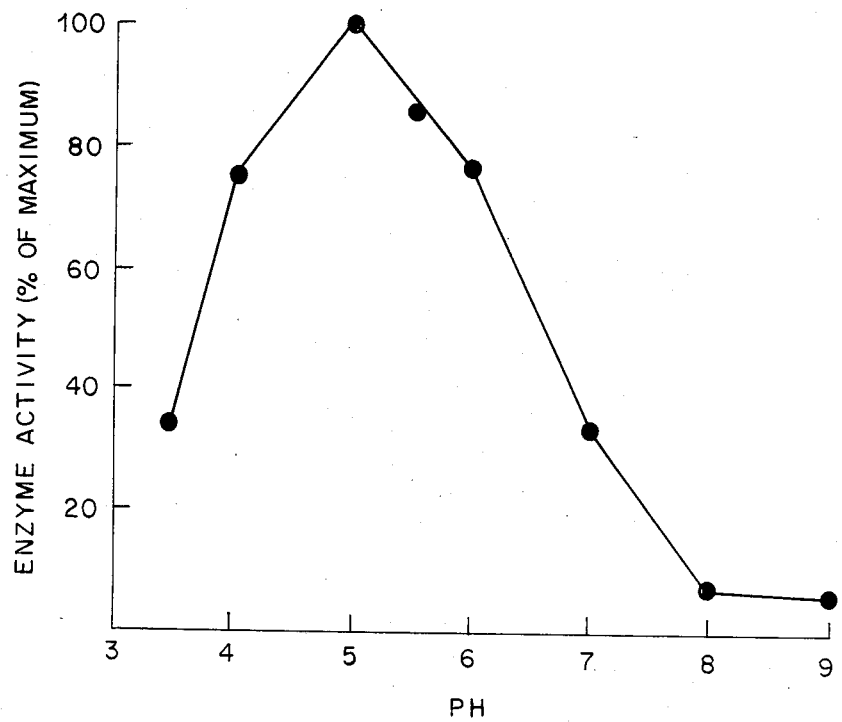
FIG. 10 shows the effect of pH on activity of xanthan depolymerase. Activity was measured at 25° C. by following the decreases in solution viscosity. The buffer solutions (0.05 M) used were: pH 3 to 6 sodium acetate buffer; pH 6 and 7, sodium phosphate buffer; pH 8 and 9. Tris-HCl buffer.

The effect of pH on xanthan depolymerase activity was studied in the pH range 3.5 to 9.0 using different buffer solutions at 0.05 M. (sodium acetate buffer pH 3.5–6; sodium phosphate buffer pH 6–7; and Tris-HCL buffer pH 8–9). Enzyme activity was measured at 25° C. with a rheometer according to the method described previously using 100 μg enzyme. The optimum pH for enzyme activity was found to be around 5 (FIG. 10).

Figure 11:
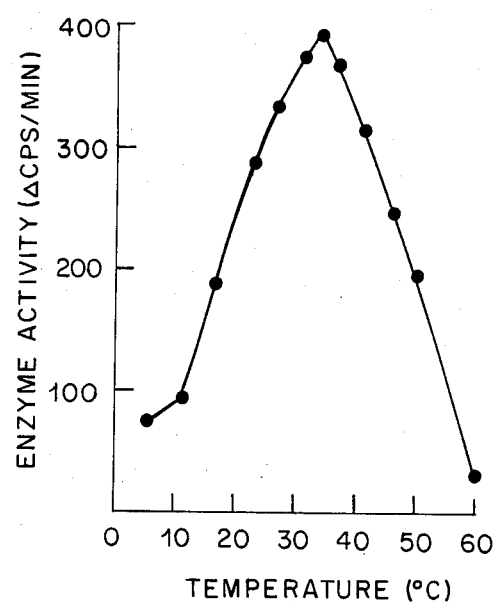
FIG. 11 shows the effect of temperature on the activity of xanthan depolymerase. The reaction mixture was equilibrated at test temperature for 5 minutes before the addition of enzyme to start the reaction. Reaction rates (as change of solution viscosity cps/min) were compared.

Temperature dependence of the activity of xanthan-depolymerase was studied between the range of 5°–60° C. The reaction mixture was equilibrated at test temperature for 5 minutes before the addition of enzyme to start the reaction. Reaction rates were compared. The optimum temperature for xanthan depolymerase activity was found to be around 30°–35° C. (FIG. 11). The activation energy calculated from the Arrhenius plot of log velocity vs. the reciprocal of absolute temperature was 6.40 Kcal/mole.

The stability of the enzyme at different temperatures was also studied. The enzyme was incubated at various temperatures for 20 min. Activity was then assayed at 25° C. The relative activities (in percent) after incubating the enzyme at different temperatures were: 100 (25° C.), 100 (30° C.), 100 (35° C.), 100 (40° C.), 33 (45° C.), 16 (50° C.), and 0 (60° C.). In addition, the enzyme was shown to be stable for at least one year at a temperature between 0° and 40° C.

Amino acid analyses were performed (with a Beckman Model 120B amino acid analyzer) after 24, 48 and 72 hour hydrolysis of 5-mg samples of protein according to the procedure of Moore and Stein.

The amino acid composition of xanthan depolymerase is presented in Table IV. The results are an average of 3 runs with different times of hydrolysis (24, 48, and 72 h). There were no sulfur-containing amino acids detected in this enzyme.

TABLE IV

Amino Acid Composition of Xanthan Depolymerase From Xanthan-Grown Culture B-15992

| Amino Acid | Number of residues/ enzyme molecule |
|---|---|
| Aspartic Acid | 52 |
| Theronine | 40 |
| Serine | 40 |
| Glutamic acid | 36 |
| Proline | 16 |
| Glycine | 32 |
| Alanine | 40 |
| Valine | 16 |
| Isoleucine | 28 |
| Leucine | 32 |
| Tyrosine | 16 |
| Phenylalanine | 8 |
| Lysine | 16 |
| Histidine | 4 |
| Arginine | 16 |
| Tryptophan | 48 |

Notes:
Tryptophan was determined spectrophotometrically (2). The molecular weight of xanthan depolymerase was estimated as 60,000 daltons.

Possible substrates including polysaccharides with known or unknown structures were tested for substrate specificity of xanthan depolymerase. Enzyme activity was measured by the release of reducing sugars. Solution viscosity assay was also performed where applicable. ZNS 63008K was a viscous heteropolysaccharide with unknown structure obtained from Kelco Company. Table V shows that xanthan depolymerase has a very narrow substrate specificity. It hydrolyzed only β-1,4-linked polymers with side chains or other substituents. The enzyme did not hydrolyze unsubstituted cellulose. The following polysaccharides, their structures not known, were not substrates for xanthan depolymerase: KID97 (high temperature stable oil field biopolymer, anionic heteropolysaccharide produced by an Alcaligenes, product of Kelco Co.); KIA 108 and KIA 112 (both are anionic heteropolysaccharides, products of Kelco Co.); Gelrite (polysaccharide consisting of uronic acid, rhamnose and glucose, product of Kelco Co.); mansan (from *Rhinocladiella mansoniei* NRRL Y-62720); indican (polysaccharide consisting of glucose rhamnose and galacturonic acid); cryptocan (polysaccharide consisting of mannose, glucuronic acid and xylose); and a polysaccharide (consisting of glucose and rhamnose) from methanol-grown *Methylocystis parvus* OBBP (11).

TABLE V

Substrate Specificity of Xanthan Depolymerase

| Substrate | Major Structure | Enzyme Activity (μmoles reducing sugar/min) |
|---|---|---|
| Kelzan | βG1 ⟶ 4G<br>\|<br>M | 3.45 (25 cps/min) |
| Carboxymethyl cellulose | βG1 ⟶ 4G | 2.40 |
| Cellulose | βG1 ⟶ 4G | 0 |
| Cellulose acetate | G1 ⟶ 4G | 0 |
| D(+) cellobiose | G1 ⟶ 4G | 0 |
| ZNS 63008K | — | 4.93 (13 cps/min) |

TABLE V-continued

Substrate Specificity of Xanthan Depolymerase

| Substrate | Major Structure | Enzyme Activity (μmoles reducing sugar/min) |
|---|---|---|
| Scleroglucan | $\beta G_6 1 \longrightarrow 3G$ <br> $\|$ <br> $\beta G 1$ | 0 |
| A. viscous | $\beta G1u1 \longrightarrow 4 \beta G1 \longrightarrow 4G$ | 0 |
| Starch | $\alpha G1 \longrightarrow 4G$ | 0 |
| Dextran | $\alpha G1 \longrightarrow 6G$ | 3.0 |
| D(+) trehalose | $\alpha G1 \longrightarrow 1G$ | 0 |

Note:
Forty μg of enzyme was used per assay.
Numbers in parenthesis were by viscosity assay where applicable.

Various chemicals including thiols, metal ions and metal-chelating agents were tested for inhibition of xanthan depolymerase activity. These chemicals (at 1 mM concentration unless otherwise stated) were added into xanthan stock solutions. Enzyme activity was assayed viscosimetrically. The enzyme activity was inhibited strongly by ferric chloride and arsenomolybdate (Table VI). Inhibition by thiol reagents and metal chelating agents was not significant. The enzyme activity was not inhibited by the following chemicals: NaCl, KCl, ferrous sulfate (5.5 mM), KOH (5.0 mM), NaOH (5.0 mM), ammonium sulfate (5.0 mm), Trizma (5.0 mM ph 8.5), Triton X-100 (4%), formaldehyde (5.5 mM), citric acid (5.5 mM), $Na_2S_2O_4$ (0.2%), antioxidants (100 ppm) such as sodium dithionite, sodium hypochlorite, chlorinated hydrocarbons (100 ppm) such as chloroform, chlorobenzene, p-chlorobenzoic acid, α-chloro-3,4-dihydroxyacetophenone, and chlorophenol. The following biocides (100 ppm) also failed to inhibit xanthan depolymerase activity: Busan 30, Busan 77, Busan 85, Busan 110, Busan 1030, sodium omadine, dow Antimicrobial 7287 (2,2-dibromo-3-nitrilopropionamide), MBT 3522 (methylene bisthiocyanate), Kathon WT (8.6% 5-chloro-2-methyl-4-isothiazoline-3-one and 2.6% 2-methyl-4-isothiazoline-3-one), 2,2-dibromo-3-nitrilopropionamide, Dowicide B (sodium trichlorophenate), and Dowicide 75 [67.5% 1-(3-chloroally)-3,5,7-triaza-1-azoniaadamantane chloride]. Xanthan depolymerase activity was not affected by an anaerobic environment.

TABLE VI

Inhibition of Xanthan Depolymerase Activity

| Inhibitor (1 mM) | % Inhibition |
|---|---|
| Thiol reagents | |
| iodoacetic acid | 0 |
| iodoacetamide | 0 |
| N—ethylmaleimide | 40 |
| p-hydroxymercuribenzoate | 40 |
| 5,5'-dithio-bis-2-n-nitrobenzoic acid | 0 |
| Metal binding agents | |
| sodium azide | 0 |
| α, α' bipyridyl | 30 |
| thiourea | 20 |
| 8-hydroxyquinoline | 0 |
| EDTA | 0 |
| 1,10-phenanthroline | 0 |
| thiosemicarbazide | 20 |
| imidazole | 30 |
| KCN | 20 |
| Metals | |
| ferric chloride (5.0 mM) | 100 |
| arsenomolybdate (4%) | 100 |

What is claimed is:

1. A method for degrading xanthan molecule comprising contacting said xanthan molecule with a mixed culture bearing the ARS Culture Collection Accession No. NRRL B-15992, wherein the contacting is conducted under aerobic conditions suitable for the growth of said first soil bacterium and for the elaboration of xanthan-degrading enzymes by said first soil bacterium, wherein said xanthan-degrading enzymes include a xanthan depolymerase which breaks the endo β-1,4-glucosidic linkage of said xanthan molecule.

2. A method for producing a supernatant which includes a salt-tolerant xanthan depolymerase comprising:
   a. culturing on a xanthan molecule-containing medium a mixed culture obtained from a culture bearing the ARS Culture Collection Accession No. NRRL B-15992, wherein said culturing is conducted under aerobic conditions suitable for the growth of said first soil bacterium and for the elaboration of xanthan depolymerase by said first soil bacterium; and
   b. recovering said supernatant which includes a xanthan depolymerase from said medium, said xanthan depolymerase capable of breaking the endo β-1,4-glucosidic linkage of said xanthan molecule.

3. The method as described in claim 2 wherein said mixed culture is said culture NRRL B-15992.

4. A method for producing a salt-tolerant xanthan depolymerase comprising:
   a. culturing a xanthan molecule-containing medium a mixed culture bearing the ARS Culture Collection Accession No. NRRL B-15992, wherein said culturing is conducted under aerobic conditions suitable for the growth of said first soil bacterium and for the elaboration of xanthan depolymerase by said first soil bacterium; and
   b. recovering said supernatant which includes a xanthan depolymerase from said medium, said xanthan depolymerase capable of breaking the endo β-1,4-glucosidic linkage of said xanthan molecule.

5. An isolated and biologically pure microbial culture of Bacillus sp. and mutants thereof obtained from the culture bearing the ARS Culture Collection Accession No. NRRL B-15992.

6. An isolated and biologically pure culture and mutants thereof bearing the ARS Culture Collection Accession No. NRRL B-15992.

* * * * *